(12) United States Patent
Biering et al.

(10) Patent No.: US 9,603,361 B2
(45) Date of Patent: Mar. 28, 2017

(54) VIRUCIDAL COMPOSITION

(75) Inventors: Holger Biering, Grevenbroich (DE); Silke Denzin, Langenfeld (DE); Friedrich Von Rheinbaben, Monheim (DE); Bernhard Meyer, Mettmann (DE)

(73) Assignee: Ecolab USA Inc., St. Paul, MN (US)

( * ) Notice: Subject to any disclaimer, the term of this patent is extended or adjusted under 35 U.S.C. 154(b) by 1307 days.

(21) Appl. No.: 12/446,952

(22) PCT Filed: Oct. 23, 2006

(86) PCT No.: PCT/EP2006/067651
§ 371 (c)(1),
(2), (4) Date: Aug. 12, 2010

(87) PCT Pub. No.: WO2008/049454
PCT Pub. Date: May 2, 2008

(65) Prior Publication Data
US 2010/0297029 A1    Nov. 25, 2010

(51) Int. Cl.
*A01N 31/02*    (2006.01)

(52) U.S. Cl.
CPC .................................. *A01N 31/02* (2013.01)

(58) Field of Classification Search
CPC .... A01N 31/02; A01N 2300/00; A01N 25/30; A01N 37/02; A01N 37/04; A01N 34/36
See application file for complete search history.

(56) References Cited

U.S. PATENT DOCUMENTS

| 4,976,953 | A | * | 12/1990 | Orr et al. ........................ 424/47 |
| 5,043,357 | A | | 8/1991 | Höffler et al. |
| 5,376,366 | A | | 12/1994 | Petchul et al. |
| 5,981,605 | A | | 11/1999 | Thomsen et al. |
| 7,470,656 | B2 | * | 12/2008 | Sherry et al. ................. 510/438 |
| 2003/0104040 | A1 | * | 6/2003 | Kirby et al. .................. 424/449 |
| 2003/0235550 | A1 | * | 12/2003 | Pan et al. .................. 424/70.16 |
| 2005/0106122 | A1 | * | 5/2005 | Gizurarson et al. ....... 424/78.38 |
| 2007/0274926 | A1 | | 11/2007 | Fuls et al. |
| 2008/0138438 | A1 | * | 6/2008 | Taylor et al. ................. 424/604 |
| 2009/0018213 | A1 | | 1/2009 | Snyder et al. |

FOREIGN PATENT DOCUMENTS

| DE | 19502456 C | * | 9/1996 |
| EP | 0465423 | | 1/1992 |
| EP | 2272339 | | 1/2011 |
| WO | WO95/13790 | | 5/1995 |
| WO | WO02/069887 | | 9/2002 |

* cited by examiner

*Primary Examiner* — Kyle Purdy
(74) *Attorney, Agent, or Firm* — Merchant & Gould P.C.

(57) ABSTRACT

The invention relates to a virucidal composition comprising based on the composition
from 80 to 99 wt-% of a $C_2$-$C_4$ monoalcohol or a mixture thereof,
from 0.1 to lower 2 wt-% of an organic acid,
from 0.1 to 1 wt-% of an alkoxylated monoglyceride and/or alkoxylated diglyceride,
wherein the pH value of the composition is from pH 3.3 to 5 and the remainder up to 100 wt-% is water.
The invention further describes a method of inactivating viruses, and a product comprising the virucidal composition and means for applying it.

18 Claims, No Drawings

VIRUCIDAL COMPOSITION

Cross Reference to Related Applications

This application is a National Stage Application of PCT/EP2006/067651, filed Oct. 23, 2006, the disclosure of which is incorporated herein by reference in its entirety.

The present invention relates to a virucidal composition, a method for the inactivation of viruses, and to products comprising the virucidal composition, and means for applying the composition.

More specifically the invention relates to a virucidal composition having a high inactivation activity against Poliovirus and SV40 virus (simian virus 40).

Skin disinfectants are used in several fields where a contamination and especially a cross contamination with bacteria and viruses should be avoided. One difficult field is the inactivation of viruses on the skin because different viruses have a different sensibility to the different disinfectants. This means whilst one type of virus is sufficiently inactivated by the disinfectant, a different virus is not inactivated. However, a disinfectant applied for virucidal disinfection should be able to inactivate all possible viruses which are present on the contaminated surface particularly on the skin and on the hands.

Two classes of viruses exist: The enveloped viruses are surrounded by a lipoid envelope and can normally be easily inactivated by compounds destroying this lipoid envelope. Therefore the inactivation of enveloped viruses is not a big problem. However, greater problems are caused by naked viruses which are non-enveloped and are quite more stable against conventional disinfectants.

Two viruses which are non-enveloped and which are very difficult to inactivate are the virus Poliovirus and SV40. Both viruses are naked viruses and do not contain a lipoid envelope.

For the classification of disinfectants European as well as national guidelines exist. Disinfectants are classified as virucidal if they can inactivate certain viruses within a certain time and to a specific extent.

The working group "virucidal property" of the Robert-Koch-Institut and the working committee "virus disinfection" of the Deutsche Gesellschaft zur Bekämpfung der Viruskrankheiten (DVV) as well as the Disinfectant Commission of the Deutsche Gesellschaft für Hygiene und Mikrobiologie (DGHM) have issued directions under which circumstances virus disinfectants can be declared as virucidal. It is made reference to Bundesgesundheitsblatt-Gesundheitsforschung-Gesundheitsschutz 2004, 47, pp. 62-66.

According to these recommendations a possibly virucidal disinfectant is tested with the following model viruses Adenovirus type 5 (strain adenoid 75), Papovavirus SV40 (simian virus 40 strain 777), Poliovirus (type 1 strain LSc-2ab), Vacciniavirus (strain Elstree). A disinfecting composition is considered as virucidal if the composition is effective against all four test viruses. The grade of inactivation (reduction of the virus titre) should be at least 4 $\log_{10}$ reduction steps in a quantitative suspension experiment if the disinfecting composition comes into contact with a contaminated surface for one minute.

For the same purpose also the European standard (EN14476 of April 2005) exists. However, in this standard only Poliovirus and Adenovirus are used as test viruses if the virucidal composition is used for hand disinfection.

The reason for the different test viruses in the European standard and the national recommendation is, that it was found that several virucidal disinfectants having a sufficient inactivation activity against Poliovirus lack a sufficient inactivation activity against SV40 virus. SV40 virus is a vacuolating virus isolated from the kidney tissue of rhesus monkeys. SV40 virus belongs to the group of Papovaviruses some of which may be potentially cancer-producing viruses.

It was found that Papovaviruses sometimes are more resistant to virucidal compositions than Polioviruses or Adenoviruses (see Rheinbaben F. von Wolff, M. H. (2002) Handbuch der Virusdesinfektion, Springer, Berlin, Heidelberg, New York, Tokyo).

If a virucidal composition is used for skin or hand disinfection it is important that the composition is skin-compatible even if the composition is used frequently. In hospitals virucidal hand disinfection is under specific circumstances carried out after each treatment of a patient. That means that a nurse working in a hospital uses the virucidal hand disinfectant twenty to forty times a day. Several virucidal disinfectants of the state of the art do not fulfil the criteria of being skin-compatible even if frequently used. These virucidal disinfectants contain high amounts of acids so that the compositions have a pH value lower than 3 or even 2. This high acidity will damage the skin especially when frequently used.

A virucidal composition for skin and hand disinfection must therefore not only fulfil the criteria to inactivate the most resistant viruses but also has to be skin-compatible even if frequently used. However, these two conditions are quite difficult to meet.

In the state of the art virucidal disinfectants are known. EP 0 692 192 A1 describes a virucidal disinfectant containing ethanol and/or methanol, and butanone. The disinfectant is used for the inactivation of Poliovirus and for skin and hand disinfection. The composition contains 90 percent or more ethanol and 0.9 percent butanone. The remainder is water. According to table 1 the reduction of the virus titre of more than 4 $\log_{10}$ units is achieved after one minute for Poliovirus. However, the activity of the composition against SV40 virus is not tested in the document.

EP 1 125 497 A2 describes a hand disinfectant comprising percarboxylic acid and alcohol. With this composition an inactivation of the virus titre of Poliovirus of greater than 4 $\log_{10}$ steps is achieved after one minute. However, the inactivation activity against SV40 virus was not investigated.

DE 196 12 057 A1 describes a disinfectant for hands comprising lower alcohols like for example ethanol in a mixture with diols like propanediol-1,2 or propanediol-1,3.

In the document an activity against Poliovirus is described. However, no information is given with respect to the activity against SV40 virus. The corresponding product on the market of the applicant Antiseptica Chem. Pharm. Prod. GmbH, Pulheim, is called Manorapid Synergy®. This virucidal composition contains 10 to 15 weight percent 1-propanol, 50 to 55 weight percent ethanol and 5 to 10 weight percent propandiol-1,2. The product has the disadvantage that after using the disinfectant on the skin the skin feels sticky due to the amount of propandiol which is remaining on the skin. Furthermore as can be seen from the patent application the activity against SV40 virus is not specified.

EP 0 176 720 A1 describes a virucidal composition against naked viruses comprising at least 70 weight percent ethanol and/or methanol and 1 to 10 percent glycerol. The application mentions that the virus titre of naked viruses is inactivated at least 4 $\log_{10}$ reduction steps. If the composition is applied on the contaminated surface. The reference refers to Poliovirus 1 strain Mahoney as test virus. However, SV40 is not mentioned in the reference. The corresponding product on the market is Sterilium Virugard® (Bode Chemie, Hamburg). The product contains 95 weight percent ethanol, glycerol, and petrol ether. However, if the product is used frequently the skin desiccates and starts itching. Furthermore no inactivation activity against SV40 virus is specified in the patent application.

U.S. Pat. No. 7,045,548 B2 relates to a virucidal composition for the treatment and/or prevention of superficial lesions or sores including canker sores, and lesions caused by viruses of the herpes viridiae and pox viridiae families.

The compositions contains 0.2 to 13 weight percent of an alcohol and an organic acid. The composition has a pH value from 2.45 to 4.6. In the claims it is specified that this composition has also an inactivation activity against Enteroviruses. However, the document does not specify that there is a 4 $\log_{10}$ reduction of the virus titre of Poliovirus and this cannot be expected because the alcohol concentration is far too low to have an effect against Poliovirus. In the experimental part of the document only the inactivation of Herpes simplex virus 1 which is an enveloped virus is shown. The document does not contain any specific data about inactivation of Poliovirus or SV40 virus.

The following documents of the state of the art are documents in which an inactivation of Poliovirus as well as SV40 virus is described.

US 2006/0193745 A1 describes a virucidal disinfectant having an activity against Poliovirus and SV40 virus. The composition comprises an alcohol like ethanol, propanol-1 or propanol-2, and an acidic phosphorous compound like for example phosphoric acid, diphosphoric acid or triphosphoric acid. Furthermore the composition comprises one or more polyalkylene glycols. The acidic phosphorous compound is present in the composition in an amount of from 0.2 to 1.5 weight percent of the disinfectant. In the examples the amount of phosphoric acid in the composition is between 0.4 to 0.8 weight percent. The amount of ethanol and propanol-1 is about 70 weight percent. It is shown that with this virucidal composition the virus titre of Poliovirus and SV40 virus is reduced after one minute by 4 $\log_{10}$ reduction steps.

However, the virucidal disinfectant, if used as a disinfectant for skin and hands, has the disadvantage that it is very acidic and therefore not skin-compatible if frequently used. Based on the amount of phosphoric acid in the composition the pH value is lower than 3. This high amount of acid is not skin-compatible, especially when the virucidal composition is frequently used on the skin.

A further virucidal composition also showing an inactivation activity against Poliovirus and SV40 virus is described in U.S. Pat. No. 5,043,357. This composition comprises high concentrations of alcohol together with organic acids in high amounts. In the examples compositions are described comprising 80 weight percent ethanol and 2 weight percent of for example lactic acid. The document states that these compositions have an inactivation activity so that the virus titre is lowered at least 4 $\log_{10}$ reduction steps within one to two minutes. These tests were carried out with Poliovirus type 1 and SV40 virus. The document only specifies a $\log_{10}$ reduction of 4 $\log_{10}$ units after a treatment of one to two minutes. However, according to the guidelines for virucidal disinfectants which were mentioned above, the $\log_{10}$ reduction has to be at least 4 $\log_{10}$ reduction steps within one minute of treatment. Hence the composition described in the reference does not have a sufficient inactivation activity especially against Poliovirus and SV40 virus. This is also confirmed by the comparative examples in the present application. Furthermore, due to the high amount of 2 weight percent of organic acid, the pH value of the composition is below 3 which means that the composition is not skin-compatible if frequently used.

The technical object of the invention is to provide a virucidal disinfectant having sufficient activity against the test viruses Poliovirus and SV40 virus, as well as having a pH value which allows to use the composition frequently on the skin without damaging the skin.

This technical object is solved by the virucidal composition comprising, based on the whole composition, from 80 to 99 wt-% of a C2-C4 monoalcohol or a mixture thereof, from 0.1 to lower 2 wt-% of an organic acid, from 0.1 to 1 wt-% of an alkoxylated monoglyceride and/or alkoxylated diglyceride, wherein the pH value of the composition is from pH 3.3 to 5 and the remainder up to 100 wt-% is water.

It was surprisingly found that compositions comprising amounts of alcohol and lower amounts of organic acid as described in the state of the art have inactivation activity against Poliovirus and SV40 virus if they are combined with a alkoxylated monoglyceride and/or alkoxylated diglyceride. The low amount of organic acids allows to keep the pH value above 3.3 in an area which is skin-compatible.

From the state of the art virucidal compositions which have an acceptable inactivation activity against Poliovirus and SV40 virus contain far higher amounts of acid and have pH values below 3.

Furthermore it was surprising that by adding a alkoxylated monoglyceride and/or alkoxylated diglyceride the inactivation activity against Poliovirus and SV40 virus is increased. This is shown in the examples of the present application. In the state of the art glycerides were only used as skin-care agents and the state of the art explicitly states that triglycerides have an inactivating effect for virucidal compositions. For example U.S. Pat. No. 5,043,357 specifies in column 3, lines 18 to 28 that due to the inactivating effect of triglycerides it is recommended to remove skin fats and after that apply a virucidal disinfectant. Furthermore it is proposed to treat the skin with suitable skin-care agents like triglycerides after the use of the virucidal agent.

The virucidal composition according to the invention is furthermore also active against other naked and enveloped viruses like Adenovirus and Vacciniavirus and therefore has a broad-range activity.

In a preferred embodiment the virucidal composition comprises 0.1 to 3 weight percent butanone, preferably 2-butanone.

In a further preferred embodiment the composition is capable of inactivating the virus titre of the viruses Poliovirus (type 1 strain LSc-2ab), Papovavirus SV40 (simian virus 40 strain 777.), Adenovirus type 5 (strain Adenoid 75), Vacciniavirus (strain Elstree) within 1 min at least 4 $\log_{10}$ reduction steps.

With "4 $\log_{10}$ reduction steps" an inactivation of the virus titre of 99.99 percentage is meant.

In a further preferred embodiment the monoalcohol used in the virucidal composition according to the invention is ethanol or mixtures of ethanol with propanol-1 or propanol-2 wherein at least 70 weight percent of the mixture of alcohols is ethanol. In a preferred embodiment the virucidal composition comprises 85 to 95 weight percent, preferably from 88 to 92 weight percent alcohol.

A further component in the virucidal composition according to the invention is the organic acid. The organic acid is preferably a carboxylic acid having one to three carboxylic groups and a carbon chain of from two to eight carbon atoms. Furthermore the carbon chain of the carboxylic acid can be substituted by one, two or three hydroxy groups.

In a preferred embodiment the organic acid is selected from the group consisting of acetic acid, citric acid, glutaric acid, glycolic acid, lactic acid, malic acid, succinic acid, valeric acid, tartaric acid, propionic acid, or mixtures thereof. In the preferred embodiment the virucidal composition according to the invention comprises from 0.2 to 1.5 weight percent, preferably from 0.3 to 0.9 weight percent of the organic acid.

The pH value of the composition according to the invention is from pH 3.3 to pH 5, preferably from pH 3.5 to pH 4.5, and most preferably from pH 3.8 to pH 4.2. The low acidity of the virucidal composition according to the invention guarantees, contrary to the state-of-the-art compositions, that the virucidal composition even if frequently used is fully skin-compatible and does not irritate the skin.

The virucidal composition according to the invention furthermore comprises an alkoxylated monoglyceride and/or alkoxylated diglyceride in an amount of from 0.1 to 1 weight percent, preferably 0.2 to 0.8 weight percent, and most preferred 0.2 to 0.5 weight percent based on the whole virucidal composition.

The glycerides preferably comprise ester groups of $C_6$ to $C_{14}$ preferably $C_8$ to $C_{12}$ carboxylic acids and the glyceride can comprise one or two identical or different ester groups. Most preferred are glycerides having ester groups of $C_8$ to $C_{10}$ carboxylic acids.

The alkoxylated monoglycerides and/or alkoxylated diglycerides are preferably alkoxylated by ethoxy and/or propoxy groups. The average grade of alkoxylation is preferably 4 to 8 mol, more preferred 5 to 7 mol and most preferred 6 mol. The grade of alkoxylation in for every single alkoxy group can vary within one molecule of the alkoxylated glyceride resulting in an average alkoxylation grade as described above.

In the most preferred embodiment the glyceride is a mixture of an ethoxylated diglyceride of the formula R—$CH_2$—CH[(O—$CH_2$—$CH_2$)$_{3-4}$—OH]—$CH_2$—R wherein R is a $C_{8-12}$ carboxylic acid ester group and an ethoxylated monoglyceride of the formula R—$CH_2$—CH[(O—$CH_2$—$CH_2$)$_{3-4}$—OH]—$CH_2$—(O—$CH_2$—$CH_2$)$_{3-4}$ OH wherein R has the same meaning as above.

The virucidal composition according to the invention is prepared by usual production processes, for example by mixing together the components of the virucidal composition in a mixing device.

The virucidal composition is normally in the form of a liquid. However, for specific uses the virucidal composition can also be in the form of a gel, a foam, or an emulsion.

In a preferred embodiment the composition can further comprise additives selected from the group consisting of stabilisers, fragrance, colorants, emulsifiers, thickeners, wetting agents, or mixtures thereof.

The virucidal composition according to the invention has a broad virucidal activity and is particularly skin-compatible. In addition it meets the recommendations of the Robert-Koch-Institut for the effectiveness of disinfectants against viruses (Bundesgesundheitsblatt-Gesundheitsforschung-Gesundheitsschutz, 2004, 42, pp. 62-66). The composition according to the invention is highly active against the described test viruses. Within a minute the virus titre of Poliovirus type 1, Papovavirus SV40, and also of Adenovirus type 5, and Vacciniavirus strain Elstree is reduced by at least 4 $\log_{10}$ reduction steps.

This is particularly important because in the state of the art for the inactivation of SV40 and Poliovirus longer treatment periods are necessary to achieve the same 4 $\log_{10}$ reduction.

The virucidal compositions according to the state of the art therefore fulfil the national German standard as well the European testing standard EN14476.

In a preferred embodiment the virucidal composition is used for the virucidal disinfection of human or animal skin. It is especially used for hand disinfection, for example in surgery or nursery. Hand disinfectants are normally used in hospitals, nursing homes, and in the surgical field. However, they can be used, too, for food processing, for example meat and/or poultry processing as well as in the processing of beverages.

With the virucidal composition according to the invention contamination or cross contamination even with highly resistant viruses like Poliovirus and SV40 virus can be avoided. Furthermore it is guaranteed that even after a short period of treatment the virus titre is sufficiently reduced. Furthermore the virucidal composition according to the invention is highly compatible to skin even if used twenty to forty times a day.

The invention further relates to a method for the inactivation of viruses comprising the steps of providing the virucidal composition according to the invention and contacting the virus-contaminated surface with the composition according to the invention for a time sufficient to reduce the virus titre at least 4 $\log_{10}$ reduction steps.

In a preferred embodiment the virus is a virus selected from the group consisting of Poliovirus, Papovavirus SV40, Adenovirus, Vacciniavirus, or mixtures thereof. It is most preferred that the virus is selected from the group consisting of Poliovirus (type 1 strain LSc-2ab), Papovavirus (SV40, simian virus 40 strain 777), Adenovirus type 5 (strain Adenoid 75), Vacciniavirus (strain Elstree) or mixtures thereof.

In a preferred embodiment the grade of inactivation of the virus titre of the viruses Poliovirus (Type 1 St. LSc-2ab), SV40 virus (simian virus 40St.), Adenovirus type 5 (strain Adenoid 75), Vacciniavirus (strain Elstree) after 1 min contact time is at least 4 $\log_{10}$ reduction steps.

The virus-contaminated surface is preferably human or animal skin. The composition according to the invention is preferably used as a virucidal hand disinfectant for frequent use.

Contrary to other virucidal compositions containing for example glycols the present virucidal composition does not leave greasy films on the disinfected skin. Such greasy films have the effect that a firm grip which may be necessary during treatment of patients is no longer ensured. Furthermore the skin feeling also becomes uncomfortable.

With the virucidal composition according to the invention no greasy-film residues are formed on the skin even if the composition is frequently applied.

The composition can be applied in liquid form, in the form of a gel, as a foam, or as an emulsion. However, it is preferred that the composition is applied in liquid form or in the form of a gel. The composition comes into contact with the skin by applying it with the hands followed by rubbing and distributing the composition evenly over the skin. The same application method can be used if the composition is in the form of a gel, in the form of a foam, or in the form of an emulsion.

A further possibility to bring the composition into contact with the skin is by spraying it onto the skin.

The invention further relates to products comprising the virucidal composition according to the invention and means for applying the composition. Preferably the means comprise a dispenser, a spray applicator, or a solid support soaked with the virucidal composition. The means are normally adapted in such a way that they can be used for liquids, gels, foams and emulsions.

If a support is used it is preferred that the support is a woven or non-woven fabric, a textile, a paper towel, cotton wool, an absorbent polymer sheet, or a sponge.

It is furthermore preferred that the virucidal composition according to the invention does not contain any peroxy groups containing compounds or phosphorous-containing acids like phosphoric acid, diphosphoric acid, triphosphoric acid, and polyphosphoric acid, or salts thereof.

The composition according to the invention and the virucidal efficiency especially against the viruses Poliovirus, SV40 virus, Adenovirus, and Vacciniavirus is illustrated by the following examples and comparative experiments.

EXAMPLES

The working group "virucidal property" of the Robert-Koch-Institut and the working committee "virus disinfection" of the Deutsche Gesellschaft zur Bekämpfung der Viruskrankheiten (DVV) as well as the Disinfectant Commission of the Deutsche Gesellschaft für Hygiene and Mikrobiologie (DGHM) have issued directions under which circumstances virus disinfectants can be declared as virucidal. It is made reference to Bundesgesundheitsblatt-Gesundheitsforschung-Gesundheitsschutz 2004, 47, pp. 62-66. The following examples were carried out according to these guidelines (DVV guidelines).

As test viruses the following viruses were used according to the recommendation of the Robert-Koch-Institut in Bundesgesundheitsblatt-Gesundheitsforschung-Gesundheitsschutz, 2004, 47, pp. 62-66. These are the viruses Poliovirus (type 1 strain LSc-2ab), Papovavirus SV40 (simian virus 40 strain 777.), Adenovirus type 5 (strain Adenoid 75), Vacciniavirus (strain Elstree).

In the tables the virus types are abbreviated as Poliovirus, SV40, Adenovirus, and Vacciniavirus.

The reduction of the virus titre was measured according to the above DVV guidelines. The contact time was one and two minutes. The tests were carried out without organic soil. The pass criterion is an achievement of 4 $\log_{10}$ reduction of the virus titre within one minute. The DVV guidelines describe in the test method that the inactivation of the virus has to be tested without organic soil containing for example proteins. In this respect it has to be noted that most of the virucidal tests carried out with substances of the state of the art are tested under soiling with serum. The present examples fulfil these criteria because the virus inactivation was measured without organic soil.

Comparative Example 1

Inactivation Effect of Ethanol of Different Concentrations on Poliovirus and SV40 Virus In example 1 the inactivation of Poliovirus and SV40 virus was investigated with different ethanol concentrations. Test were carried out without organic soil. The results show the $\log_{10}$ reduction of the virus titre after one minute contact time.

TABLE 1

| EtOH [wt.-%], remainder water | Poliovirus [$\log_{10}$ reduction] | SV40 virus [$\log_{10}$ reduction] |
| --- | --- | --- |
| 70 | 1.0 | 3.5 |
| 75 | 1.3 | 2.9 |

TABLE 1-continued

| EtOH [wt.-%], remainder water | Poliovirus [$\log_{10}$ reduction] | SV40 virus [$\log_{10}$ reduction] |
| --- | --- | --- |
| 80 | 3.1 | 3.0 |
| 85 | 3.4 | 3.5 |
| 90 | 4.4 | 2.9 |

It can be seen that the inactivation of Poliovirus and SV40 virus to a sufficient extent cannot be achieved by using ethanol in a concentration between 70 and 90 weight percent. It can only be seen that by using 90 weight percent ethanol the Poliovirus reduction after one minute is 4.4. However, by using this concentration of ethanol the SV40 reduction of 2.9 is not satisfactory and does not fulfil the respective recommendations for virucidal compositions. From the example can be concluded that ethanol alone cannot be used as a virucidal composition with a broad inactivation efficiency.

Example 2

Composition According to Invention

In the following examples compositions according to the state of the art comprising ethanol and lactic acids were tested against the composition according to the invention containing ethanol, lactic acid, and a mixture of PEG-6, as well as a triglyceride. The following table 2 shows the ingredients of the composition.

TABLE 2

| components [wt.-%] | Ex 1(c) | Ex 2(c) | Ex 3 |
| --- | --- | --- | --- |
| EtOH | 90 | 90 | 90 |
| lactic acid | — | 0.6 | 0.6 |
| PEG-6 capric/caprylic acid/glyceride | — | — | 0.3 |
| fragrance | 0.2 | 0.2 | 0.2 |
| pH | 6.5 | 3.8 | 4.0 | the remainder up to 100 wt.-% is water,
c = comparative example; all numbers given in wt.-%

The following table 3 shows the results of the reduction of the virus titre after one minute contact time.

TABLE 3

| $\log_{10}$ reduction after 1 min. contact | Ex 1(c) | Ex 2(c) | Ex 3 |
| --- | --- | --- | --- |
| Polio | 3.0 | 3.1 | >4.0 |
| SV40 | 0.9 | 1.3 | >4.0 |
| Adenovirus | >4.0 | >4.0 | >4.0 |
| Vacciniavirus | >4.0 | >4.0 | >4.0 |

It can be seen that Adenovirus and Vacciniavirus are inactivated in a sufficient way. The virus titre of these viruses is reduced more than 4 $\log_{10}$ reduction steps after one minute contact time. However, differences can be seen in relation to the inactivation of Poliovirus and SV40 virus. Comparative example 1 does not show a sufficient inactivation of Poliovirus and SV40 virus. This confirms the finding in the state of the art that only by using higher concentrations of organic acids a sufficient reduction of Poliovirus is possible. Example 2 shows that addition of an organic acid in skin compatible amounts increases efficacy against SV40 virus and Poliovirus, but efficacy is still not sufficient. Example 3 shows that by using the composition according to the invention comprising ethanol, lactic acid, and a mixture of PEG-6, and a triglyceride a sufficient inactivation can be achieved with Poliovirus as well as with SV40 virus.

The following table 4 shows the results for two minutes contact time.

TABLE 4

| $\log_{10}$ reduction after 2 min. contact | Ex 1(c) | Ex 2(c) | Ex 3 |
|---|---|---|---|
| Polio | 3.2 | 3.2 | >4.0 |
| SV40 | 1.4 | 1.8 | >4.0 |
| Adenovirus | >4.0 | >4.0 | >4.0 |
| Vacciniavirus | >4.0 | >4.0 | >4.0 |

Also from table 4 the results of table 3 are confirmed. Even with a contact time of two minutes the compositions according to the comparative examples 1 and 2 are not able to sufficiently inactivate SV40 virus. This shows that even after longer contact times a composition containing low amounts of organic acids and no mixtures of PEG with triglycerides are not able to sufficiently inactivate SV40 virus.

Contrary to that it can be seen that example 3 which shows the composition according to the invention reduces the virus titre of both Poliovirus and SV40 virus by more than 4 $\log_{10}$ reduction steps within one minute contact time.

The invention claimed is:

1. A method for the inactivation of viruses comprising applying a composition to a virus contaminated surface for a time sufficient to reduce the virus titre at least 4 $\log_{10}$ steps, the composition comprising:
   antimicrobial components;
   optionally one or more additives selected from stabilizers, fragrance, colorants, emulsifiers, thickeners, wetting agents, or mixtures thereof; and
   water,
   wherein the antimicrobial components consist of, by weight of the composition, from 80 to 99 wt-% of a $C_2$-$C_4$ monoalcohol or a mixture thereof, from 0.1 to about 2 wt-% of an organic acid, from 0.1 to 1 wt-% of an alkoxylated monoglyceride or alkoxylated diglyceride, and from about 0.1 to about 3 wt. % of butanone,
   wherein the pH value of the composition is from pH 3.3 to 5, and
   wherein the virus contaminated surface is human or animal skin.

2. The method of claim 1, wherein the virus is selected from the group consisting of Poliovirus, Papovavirus SV40, Adenovirus, Vacciniavirus, and mixtures thereof.

3. The method of claim 1, wherein the virus is selected from the group consisting of Poliovirus (type 1 strain LSc-2ab), Papovavirus (SV40, simian virus 40 strain 777), Adenovirus type 5 (strain Adenoid 75), Vacciniavirus (strain Elstree), and mixtures thereof.

4. The method of claim 1, wherein the grade of inactivation of the virus after 1 min contact time is at least 4 $\log_{10}$ reduction steps.

5. The method of claim 1, wherein the composition is used as virucidal hand disinfectant for frequent use.

6. The method of claim 1, wherein the composition is applied by spraying.

7. The method of claim 1, wherein the organic acid is selected from the group consisting of acetic acid, citric acid, glutaric acid, glycolic acid, lactic acid, malic acid, succinic acid, valeric acid, tartaric acid, propionic acid, and mixtures thereof.

8. The method of claim 1, wherein the composition comprises from 0.2 to 1.5 wt-% organic acid.

9. The method of claim 1, wherein the composition comprises a mixture of an ethoxylated monoglyceride and an ethoxylated diglyceride.

10. The method of claim 1, wherein the ethoxylated monoglyceride has the following structure:

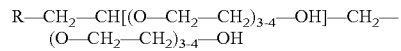

wherein R is a $C_{8-12}$ carboxylic acid ester.

11. The method of claim 1, wherein the ethoxylated diglyceride has the following structure:

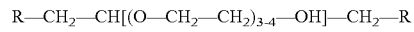

wherein R is a $C_{8-12}$ carboxylic acid ester.

12. The method of claim 9, wherein the ethoxylated monoglyceride has the following structure:

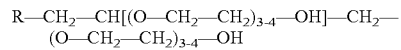

wherein R is a $C_{8-12}$ carboxylic acid ester; and the ethoxylated diglyceride has the following structure:

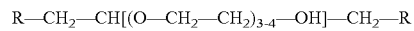

wherein R is a $C_{8-12}$ carboxylic acid ester.

13. The method of claim 1, wherein the composition is in form of a gel, a foam, or an emulsion.

14. The method of claim 1, wherein the composition comprises further additives selected from the group consisting of stabilizer, fragrance, colorants, emulsifier, thickener, wetting agents, and mixtures thereof.

15. The method of claim 1, wherein the butanone is 2-butanone.

16. The method of claim 1, wherein the composition has a pH from about 3.8 to about 4.2.

17. The method of claim 1, wherein the composition is used as a virucidal hand sanitizer.

18. The method of claim 17, wherein the composition can be used up to 40 times per day without damaging the skin.

* * * * *